United States Patent
Sheffy

(10) Patent No.: US 9,849,022 B2
(45) Date of Patent: Dec. 26, 2017

(54) SYSTEM AND METHOD FOR USE IN ERECTILE DYSFUNCTION CONDITIONS

(71) Applicant: Jacob Sheffy, Zichron Ya'akov (IL)

(72) Inventor: Jacob Sheffy, Zichron Ya'akov (IL)

( * ) Notice: Subject to any disclaimer, the term of this patent is extended or adjusted under 35 U.S.C. 154(b) by 52 days.

(21) Appl. No.: 14/404,240

(22) PCT Filed: May 21, 2013

(86) PCT No.: PCT/IL2013/050440
§ 371 (c)(1),
(2) Date: Nov. 28, 2014

(87) PCT Pub. No.: WO2013/175473
PCT Pub. Date: Nov. 28, 2013

(65) Prior Publication Data
US 2015/0257921 A1     Sep. 17, 2015

Related U.S. Application Data

(60) Provisional application No. 61/649,380, filed on May 21, 2012.

(51) Int. Cl.
*A61F 5/00* (2006.01)
*A61F 5/41* (2006.01)

(52) U.S. Cl.
CPC .......... *A61F 5/41* (2013.01); *A61F 2005/412* (2013.01); *A61F 2005/415* (2013.01)

(58) Field of Classification Search
CPC ................ A61F 5/41; A61F 2005/412; A61F 2005/415; A61H 19/00; A61H 19/30; A61H 19/32

(Continued)

(56) References Cited

U.S. PATENT DOCUMENTS

| 4,407,275 A | 10/1983 | Schroeder |
| 5,501,650 A | 3/1996 | Gellert |
| 2003/0004423 A1* | 1/2003 | Lavie .................. A61B 5/1073 600/500 |

FOREIGN PATENT DOCUMENTS

| CN | 2268503 Y | 11/1997 |
| CN | 1439353 A | 9/2003 |

(Continued)

*Primary Examiner* — John Lacyk
(74) *Attorney, Agent, or Firm* — Browdy and Neimark, P.L.L.C.

(57) ABSTRACT

A non-invasive system for inducing penile blood vessel and erectile tissue volume changes, comprising a cylindrical socket, having interior walls and an open end with a circumferential sealing element, and a control unit connected to pressure pumps are provided, wherein a compartment defined by the sealing element and the interior walls is in a state of positive pressure, or in a state of sub-atmospheric pressure. Pressure reservoirs, connectable to the compartment and to the pressure pumps, and mechanical switching elements connected to the pressure reservoirs are provided. Measuring elements are also provided, wherein the control unit is capable of receiving a signal from the measuring elements and determining a time, rate and shape of measured pulse-waves, and wherein the control unit is gated by the measuring element to control the switching elements to switch connectivity of the compartment to the reservoir and alternately switch the compartment between states.

20 Claims, 15 Drawing Sheets

(58) Field of Classification Search
USPC .................................................. 600/38–41
See application file for complete search history.

(56) References Cited

FOREIGN PATENT DOCUMENTS

| | | | |
|---|---|---|---|
| CN | 201131882 | Y | 10/2008 |
| CN | 101658450 | A | 3/2010 |
| WO | 9827898 | A1 | 2/1998 |
| WO | 2011045632 | A1 | 4/2011 |

* cited by examiner

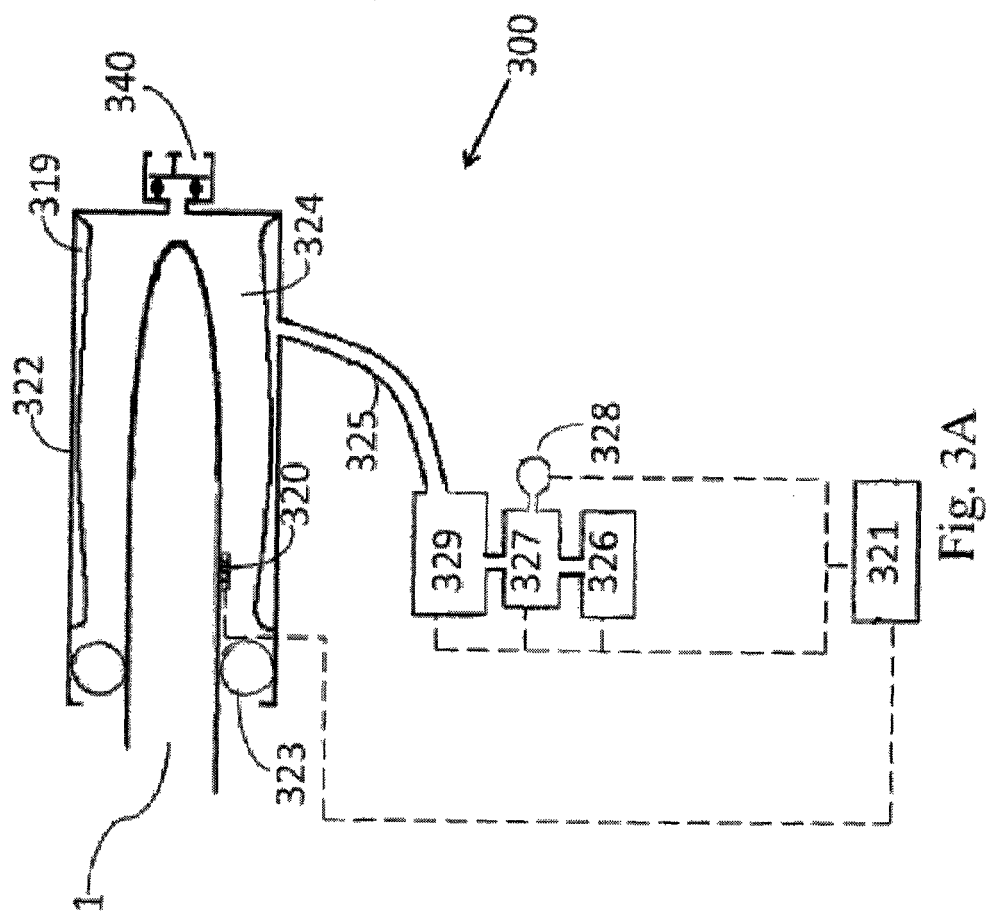

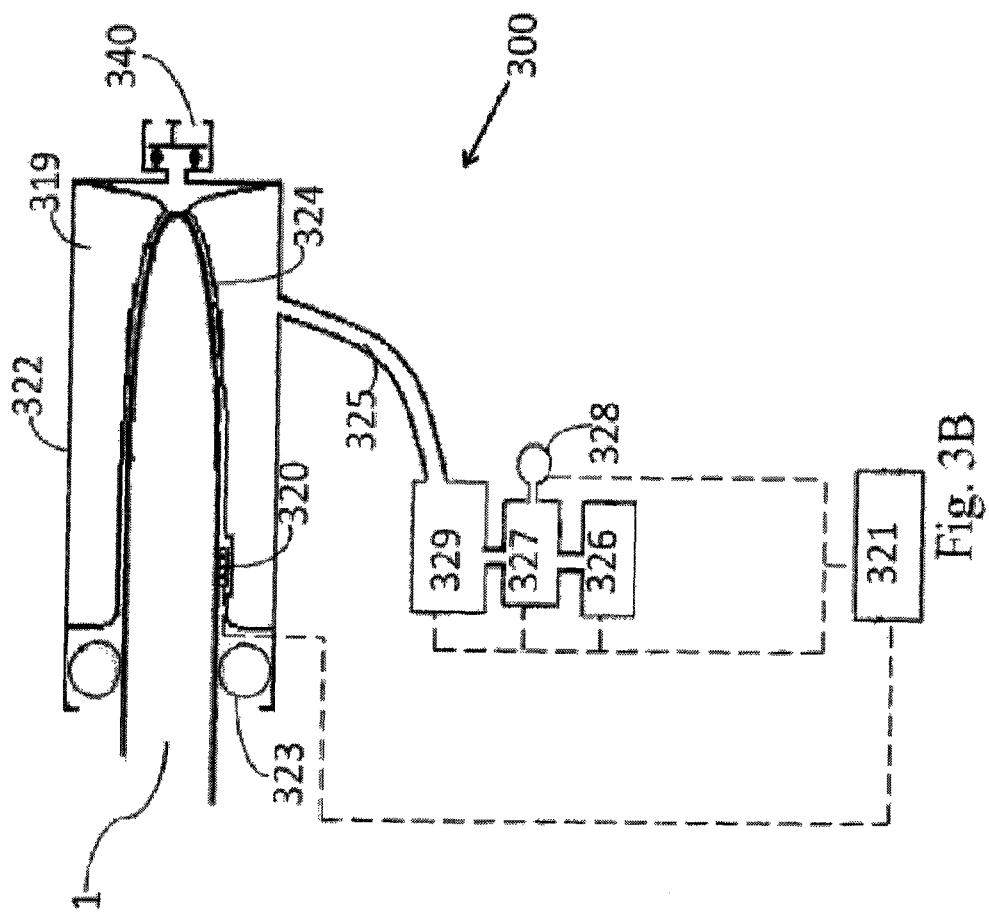

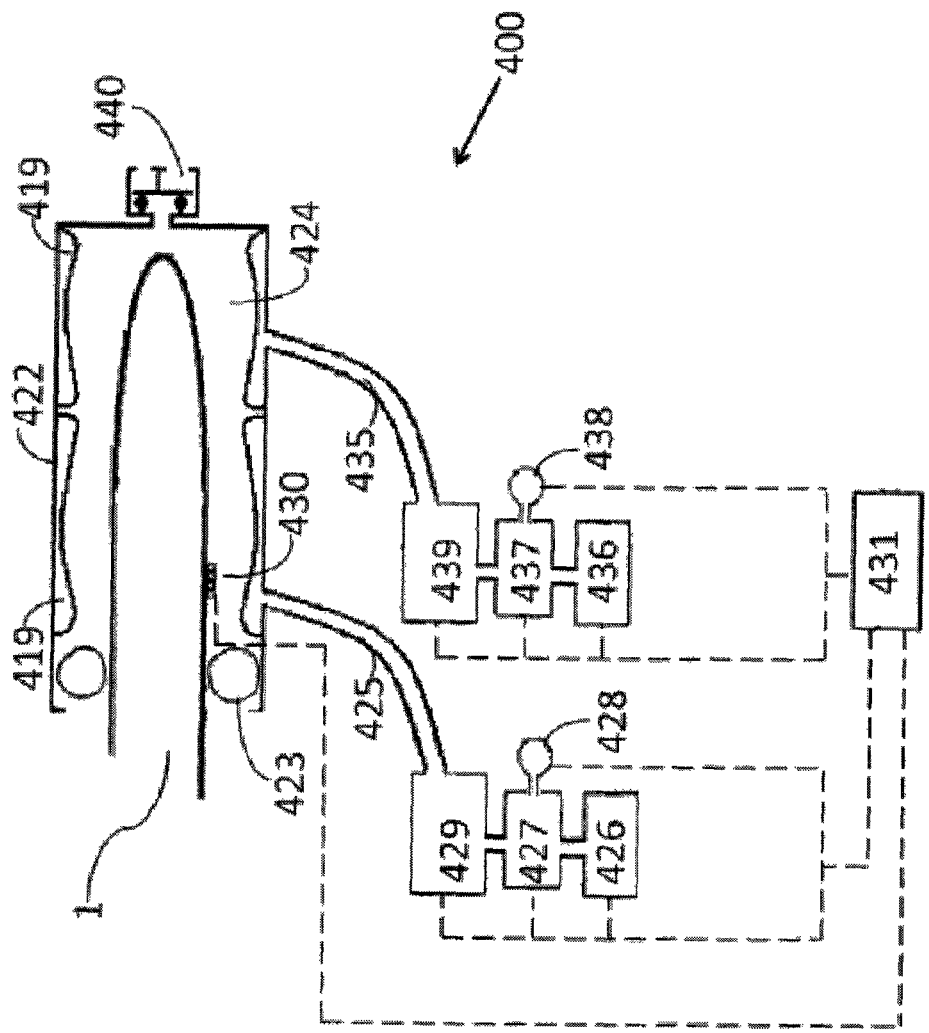

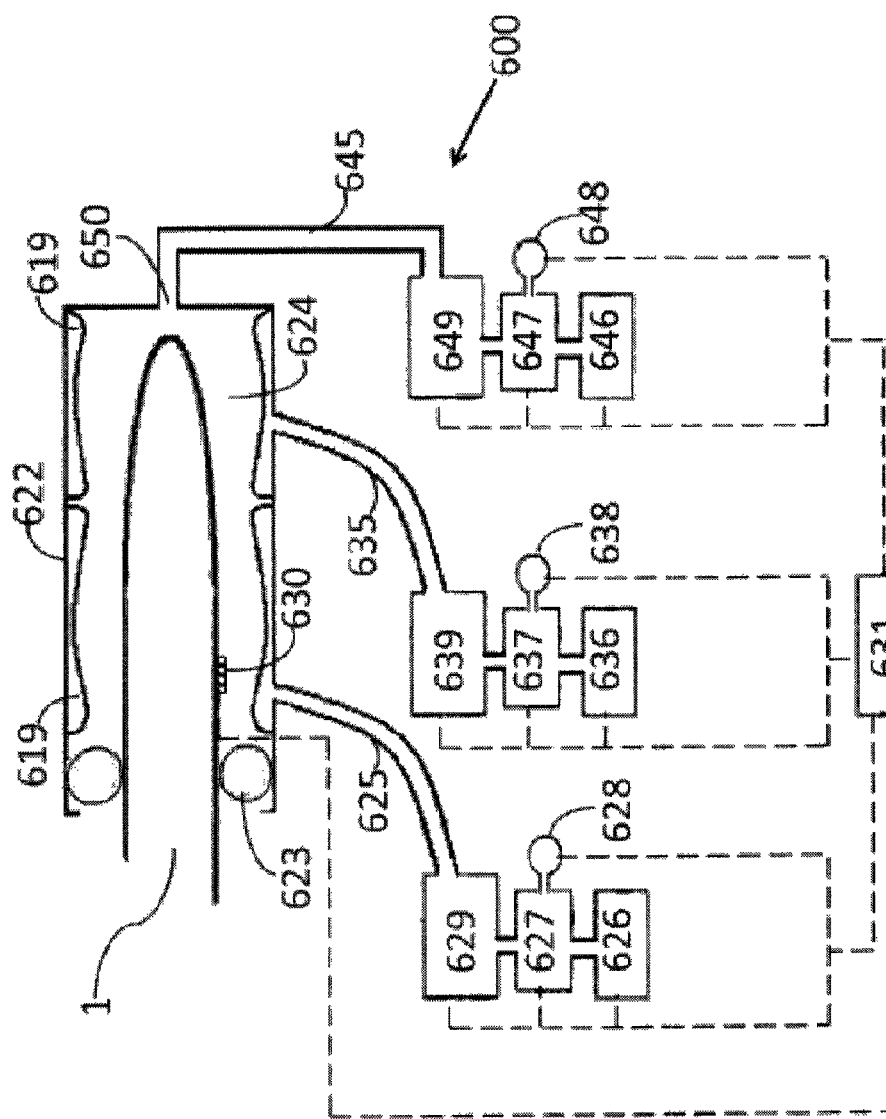

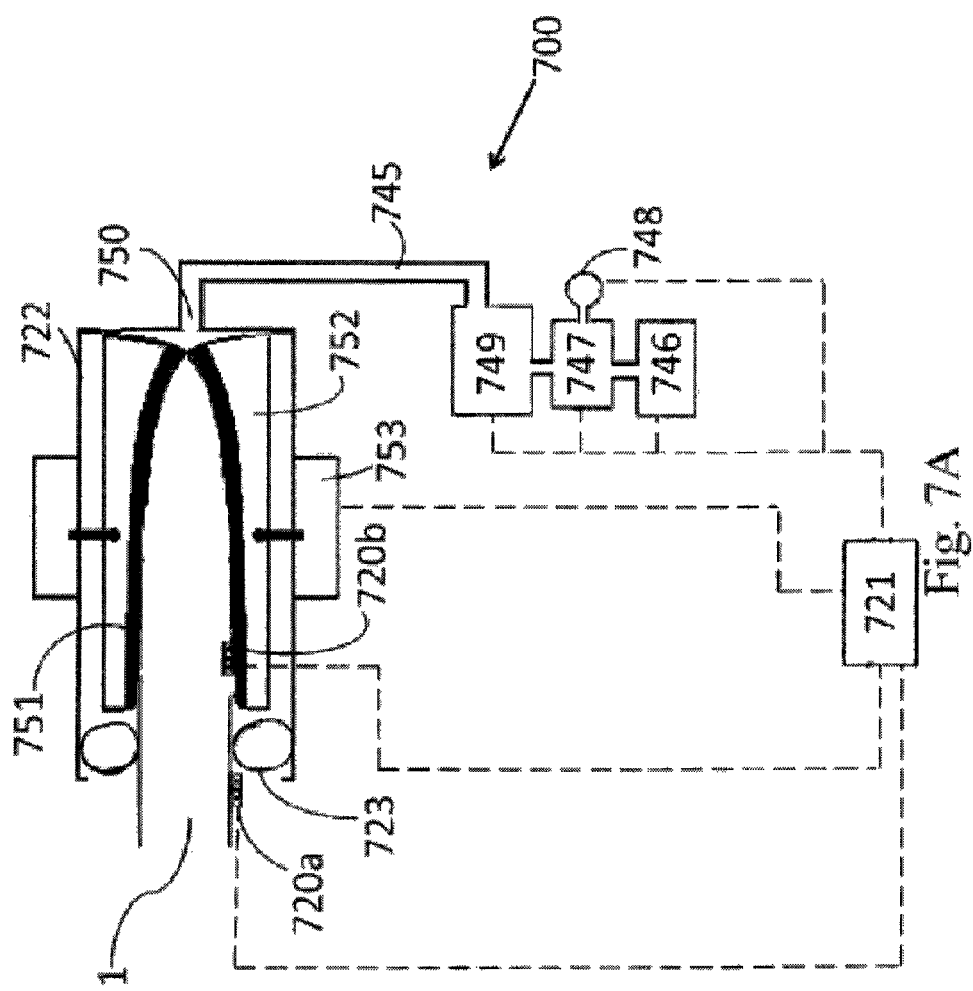

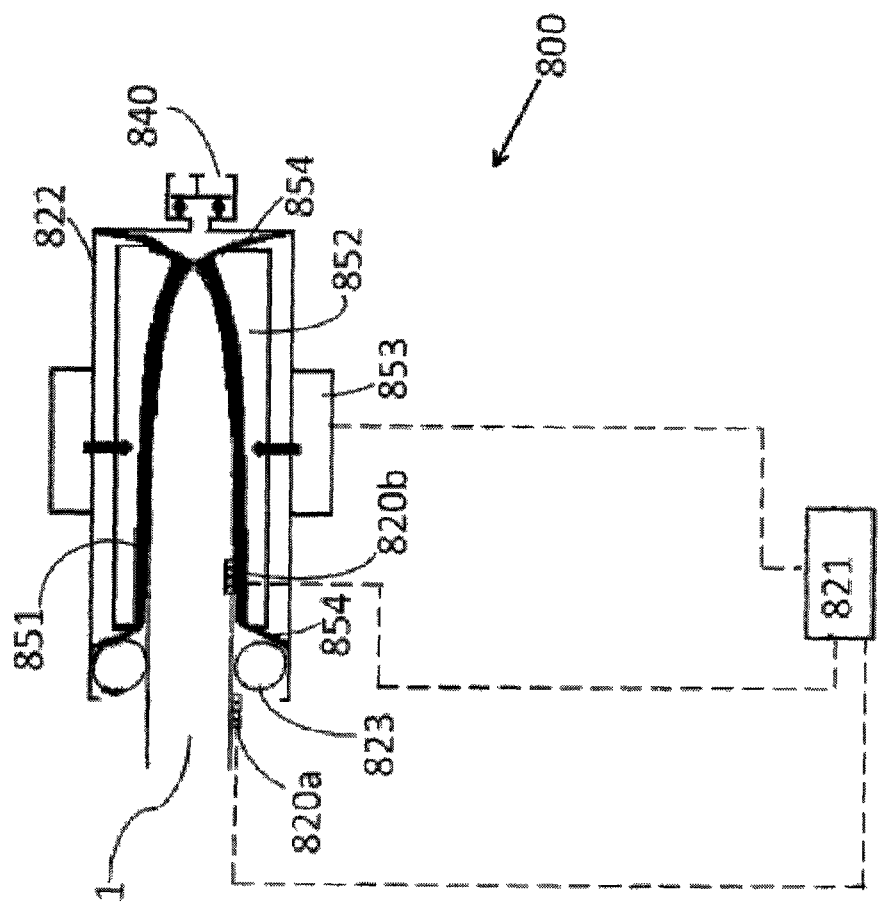

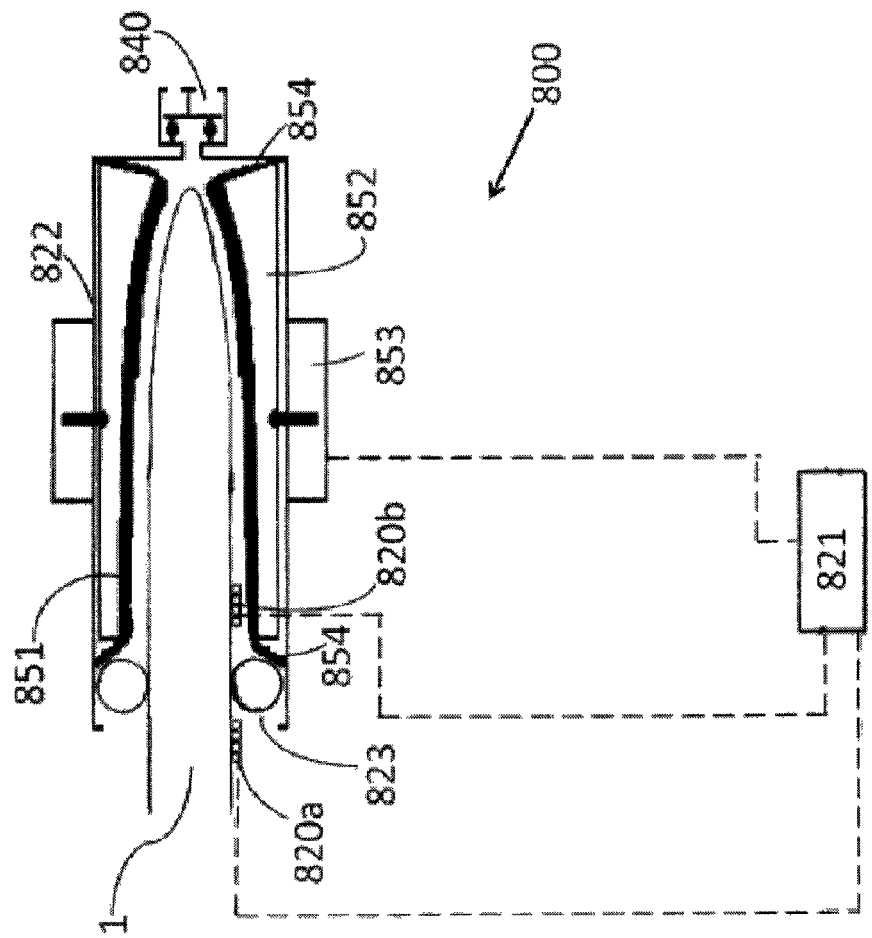

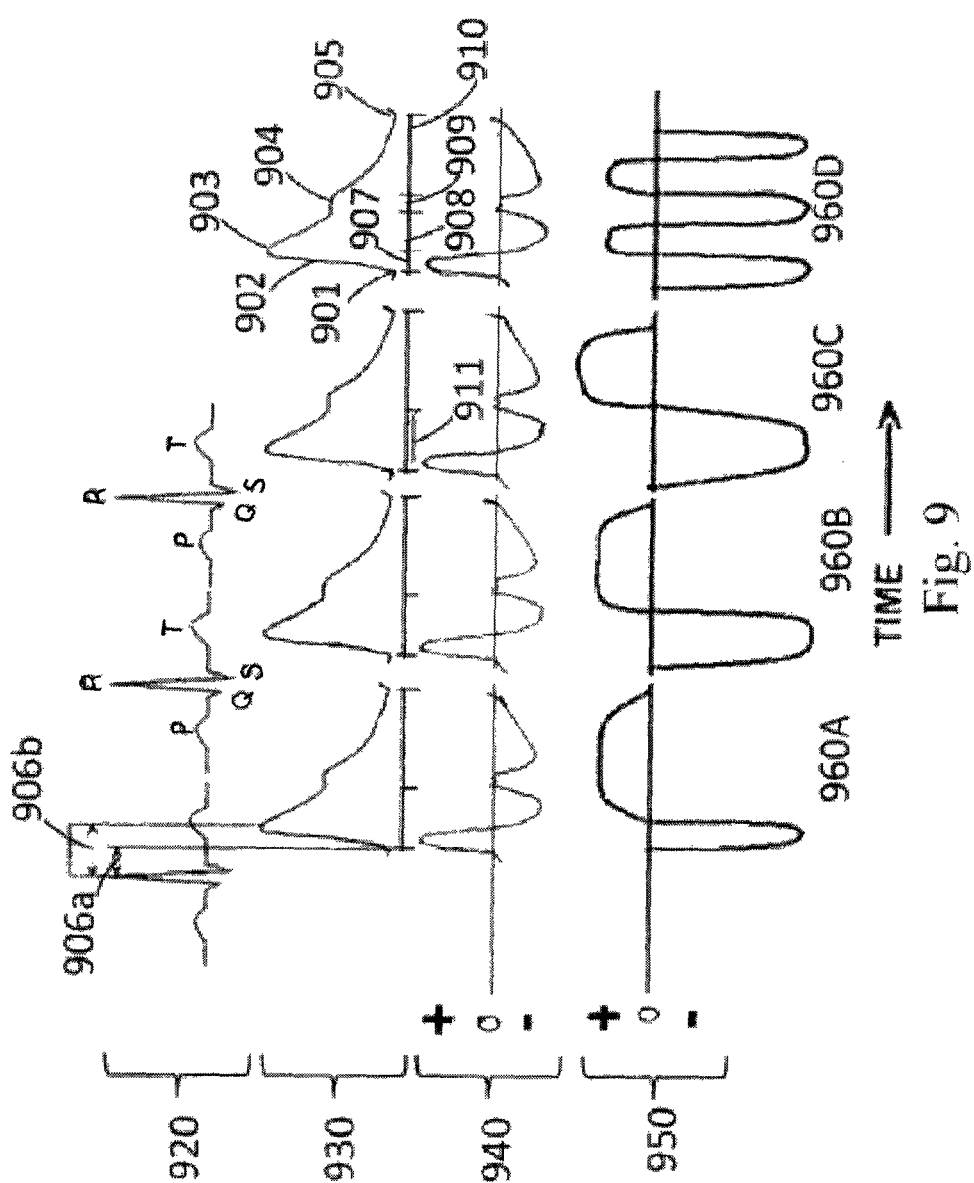

SYSTEM AND METHOD FOR USE IN ERECTILE DYSFUNCTION CONDITIONS

CROSS REFERENCE TO RELATED APPLICATIONS

This patent application is a U.S. National Phase filing of commonly owned PCT Application No. PCT/IL2013/050440, filed May 21, 2013, which is based on and claims the benefit of the filing date of U.S. Provisional Patent Application Ser. No. 61/649,380, filed May 21, 2012, both which are incorporated herein by reference in their entirety.

FIELD OF THE INVENTION

The present invention relates to a system and method for use in cases of erectile dysfunction. More particularly, the present invention relates to a system and method to effect changes in the filling volume and filling dynamics of penile blood vessels and the spongy penile erectile tissues, and for improving the functional erectile function of the penis, in a cyclic manner related to a measured pulse.

BACKGROUND OF THE INVENTION

Erectile dysfunction (ED) is an extremely common sexual dysfunction characterized by the inability to develop or maintain an adequate erection of the penis during sexual performance, or during rapid eye movement (REM) stage sleep. It may be primarily vasogenic (aka organic, when REM stage sleep related adequate erections do not occur), psychogenic (when REM stage sleep related adequate erections do occur), or mixed vasogenic and psychogenic in origin.

A penile erection is ultimately the outcome of the hydraulic effect of blood entering and being retained in the inflated erectile sponge-like bodies within the penis. The physiology of normal erectile function and pathophysiology of ED are highly complex and multifactoral in nature, involving amongst other determinants, local tissue factors, autonomic nervous system regulation, endocrine factors and higher mental function, the complex interactions of which are not yet fully elucidated, and are the subjects of continuously ongoing study. While a comprehensive review of this subject is beyond the scope of this description, the essential clinical condition of ED is indicated when a satisfactory erection is consistently difficult to produce and maintain.

There are various possible causes and co-morbidities associated with ED, however the major cause of vasculogenic ED is related to clinical or sub-clinical atherosclerotic, and degenerative conditions of the vasculature of the penis, and or loss of elasticity of the penile spongy tissues, which are considered mostly responsible for generating organic erectile dysfunction These degenerative conditions are widely considered to be causally related, at least in part, to a state of endothelial dysfunction.

Currently, treatment of erectile dysfunction is limited to on demand solutions which usually consist of drug therapy, or the use of a variety of physical approaches, all of which are giving a limited time solution to help in achieving intercourse within a short period of time i.e., between 30 min to few hours. There is no reasonable treatment for the chronic condition.

Drug treatment is most often based on the use of the phosphodiesterase type 5 (PDE5), inhibitors (the first of which was sildenafil or Viagra), a class of drugs known to improve erectile function. These drugs also improve endothelium-dependent vasodilation through increased NO production. Less commonly, treatment can involve prostaglandin tablets in the urethra, injections into the penis, a penile prosthesis, a penile pump or vascular reconstructive surgery.

Often such pharmacological methods fail, or are contraindicated in many men, including those diagnosed with heart conditions, hypertension, glaucoma and many other conditions, and may also carry increased risk of strokes, particularly in those suffering from arrhythmias, or those having suffered a previous heart attack or stroke, difficulty breathing, vision problems, headaches and flushing. Furthermore they often cause side effects such as headaches, gastrointestinal upsets, diarrhea, blurred vision, urinary tract infections, or pathologically excessively long-term erections (priapism), amongst others.

Physically based treatment methods most typically involve the use of a purpose-designed external vacuum pump to attain erection and maintain it to approximately 30 min, with a separate compression ring fitted to the penis to maintain it. Such device helps draw blood into the penis by applying constant negative pressure. This type of device is sometimes referred to as penis pump and is used just prior to sexual intercourse. Several types of vacuum therapy devices are available with a doctor's prescription.

These pumps should be distinguished from other penis pumps (supplied without compression rings) which, rather than being used for temporary treatment of impotence, are claimed to increase penis length if used frequently, or vibrate as an aid to masturbation. More drastically, inflatable or rigid penile implants may be fitted surgically.

The commercially available pumps to treat erectile dysfunction have several disadvantages: They require 10 to 30 minutes to achieve and maintain an erection. The constriction ring needs to be very tight on many men in order to maintain the erection, and this can be painful. In addition, the erection men achieve using a vacuum pump is less aesthetically pleasing than one that occurs using other methods. This is because the blood that is drawn into the penis when using the vacuum is mostly from the veins and has low levels of oxygen, which makes the penis bluish or gray rather than pink. The erection is also cooler in temperature than one that is obtained "normally," because the blood in the penis is mainly from the veins, not the arteries, which is warmer.

Several mechanical devices have been used in erectile dysfunction; U.S. Pat. No. 5,501,650, "Automated masturbatory device", describes a device that generates back and forth strokes to the penis caused by positive and negative applied pressures within the system when applied to the heavily lubricated penis, causing displacements of the penis relative to the apparatus, for the purpose of sexual stimulation. The timing of the cyclic pressure swings is predetermined and unrelated to the cardiac or vascular pulsatile cycle.

U.S. Pat. No. 4,407,275, "Artificial erection device", describes a semi-rigid annular ring having individual expandable chambers on the internal wall that are distended separately by fluid pressure. A multi-port flexible conduit connected to the ring has individual ports for each chamber. Fluid pressure is supplied through the conduit manually by a bulb or electrically by a pump through a circular valve plate allowing the chambers to expand and contract in linear sequence. When a penis is placed into the ring and fluid pressure is applied, blood is forced to the end of the organ through the successive expansion and contraction of the bellows due to positive and negative pressures supplied to the apparatus in wave fashion mechanically creating an erect condition of the organ.

However, in the device described in U.S. Pat. No. 4,407,275 the timing of the cyclic pressure swings is unrelated to the cardiac cycle, and the method is not intended to improve endothelial condition of the penile arteries.

It is an objective of the present invention to provide an externally applied non-invasive system for inducing vascular caliber changes in the blood vessels of the penis, and tissue volume changes of the sponge like erectile tissues unique to the penis (principally the corpora cavernosa and corpus spongiosum), to improve endothelial function of the penile blood vessels and to improve the elasticity of the sponge like erectile tissues of the penis, and thereby to improve erectile dysfunction.

SUMMARY OF THE INVENTION

According to one aspect, a method of treating a condition of erectile dysfunction of a subject is provided, the method comprising inducing cyclic augmented penile blood volume changes in the penis of the subject.

Said penile blood volume changes may be penile blood vessel changes and penile erectile spongy tissue volume changes.

Said induced cyclic augmented penile blood vessel and penile erectile spongy tissue volume changes may be effective to elicit improved endothelial function, and increased tissue elasticity.

Said cyclic augmented penile blood volume changes may be induced by application of alternating phases of subatmospheric pressure, and above atmospheric pressure, or mechanical force applied to the penile tissue surface.

Said alternating of phases of sub-atmospheric pressure, and above atmospheric pressure or applied force to the penile tissues, may be gated by the timing and/or amplitude and/or rate and/or shape of a peripheral pulse-wave of the subject.

In some embodiments, said pulse-wave amplitude cycle is preceded by a predetermined delay period by ECG signal markers.

The time delay between said ECG signal markers and said pulse-wave amplitude cycle may be determined from an estimated pulse transit time.

According to another aspect, a non-invasive system for inducing penile blood vessel and penile erectile tissue volume changes is provided, the system comprising:

a cylindrical socket, having interior walls an open end;

at least one circumferential sealing element within the socket, wherein a pressurizable compartment is defined by the sealing element and the interior walls;

a control unit and a processing unit;

at least one pressure pump operationally connected to the control and processing unit, wherein the compartment when sealed is in one of two states: a first state wherein the compartment is in positive pressure, and a second state, wherein the compartment is in sub-atmospheric pressure;

at least one pressure reservoir, each reservoir fluidly connectable to said compartment and to one of the pressure pumps;

at least one mechanical switching element operationally connected to the control and processing unit and to at least one of the pressure reservoirs;

at least one measuring element capable of measuring a pulse-wave or a cardiac cycle, wherein: the control and processing unit is capable of receiving a signal from the measuring elements and determining a time, rate and shape of pulse-waves, and wherein said control and processing units are gated by the at least one measuring element to control said mechanical switching elements such as to switch fluid connectivity of the pressurizable compartment to the reservoirs and alternately switch the sealed compartment between the first state and the second state.

The control unit and the processing units may be integrated units.

The term "cylindrical" is not to be strictly construed; other shapes that allow a penis to be comfortably inserted into the socket will serve just as well and are generally referred to as "cylindrical".

In some embodiments the non-invasive system further comprises a pressure or force application controlling mechanism operationally connected to the control and processing unit and the measuring elements, and programmed to control the positive pressure or applied force and sub-atmospheric pressure according to amplitude of the measured pulse or pulse-wave.

In some embodiments the switching of pressures is gated by the onset of a systolic upstroke as measured by said measuring element.

In some embodiments the switching of pressures or applied force is gated by a fixed time delay from an ECG-R wave as predetermined with respect to the measuring elements.

In some embodiments the switching is programmed to occur at a predetermined fraction of a predetermined time period from the onset of the systolic upstroke.

In some embodiments the switching is programmed to continue until a predetermined fraction of the peripheral pulse wave cycle is reached.

In some embodiments the control and processing unit is set to control a period of pressure holding before the pressure or force application switching.

In some embodiments the switching of pressures is programmed to be carried out at a rate higher than the measured pulse rate.

Some embodiments further comprise an inflatable annular cuff fluidly connected to said at least one pressure pump.

Some embodiments further comprise a one-way valve fluidly connectable to said compartment, and capable of removing air trapped by said inflatable annular cuff.

Some embodiments further comprise at least two inflatable annular cuffs fluidly connected to said at least one pressure pump, or at least one force applying means, and capable of sequential timing of the respective pressurization of the cuffs, coordinated by said processor in the control and processing unit.

Some embodiments further comprise a one-way valve fluidly connected to said compartment, and capable of removing air trapped by said inflatable annular cuff.

Some embodiments further comprise a circumferential sleeve-like extension to the sealing element, wherein the circumferential sleeve-like extension is connected to the at least one measuring element.

In some embodiments the extension further comprises a skin-adhesive.

Some embodiments further comprise said at least one measuring element comprises a first and a second pulse sensor wherein the first pulse sensor is placed within the compartment, and the second pulse sensor is placed outside the compartment, and the control unit is programmed such that when an attenuation of a pulse signal is recorded by the first sensor, relative to the signal recorded by the second sensor, the control unit commands the pumps to cease applying positive pressure or force to the compartment.

In some embodiments said at least one measuring element comprises a first and a second pulse sensor wherein the first pulse sensor is placed within the compartment, and the second pulse sensor is placed outside the compartment, and the control unit is programmed such that when a amplitude of a pulse signal is recorded by the first sensor exceeds a predetermined value, relative to the signal recorded by the second sensor, the control unit commands the pumps to cease applying sub-atmospheric pressure to the compartment.

According to another aspect, inducing cyclic augmented penile blood volume changes in a penis of a subject is provided, the inducing comprising:
providing a cylindrical socket, having interior walls an open end, at least one circumferential sealing element within the socket, a means for inducing cyclic augmented penile blood volume changes in the penis of the subject; wherein a pressurizable compartment is defined by the sealing element and the interior walls;
a control and processing unit; at least one mechanical switching element operationally connected to the control and processing unit and at least one measuring element capable of measuring a pulse-wave or a cardiac cycle;
sealing the compartment by inserting the penis through the sealing element into the socket;
operationally coupling the measurement elements to the subject;
sending at least one signal from the measuring elements to the control and processing unit, and determining a time, rate and shape of pulse-waves from the subject;
the at least one measuring element gating said control and processing unit to alternately apply with the means for inducing cyclic augmented penile blood volume changes, such as to apply positive force or pressure to the penis, and sub-atmospheric pressure to said compartment, such as to apply sub-atmospheric pressure to the penis.

In some embodiments, said means for inducing cyclic augmented penile blood volume changes in the penis of the subject is for example an at least one pressure pump operationally connected to the control and processing unit; and the providing further comprises the providing of: at least one pressure reservoir, each reservoir fluidly connectable to said compartment and to one of the pressure pumps; at least one mechanical switching element operationally connected to the control and processing unit and to at least one of the pressure reservoirs, and at least one measuring element capable of measuring a pulse-wave or a cardiac cycle.

In some embodiments said means for inducing cyclic augmented penile blood volume changes in the penis of the subject is an at least one force applicator operationally connected to the control and processing unit, and at least one pressure pump operationally connected to the control and processing unit; and the providing further comprises the providing of: at least one pressure reservoir, each reservoir fluidly connectable to said compartment and to one of the pressure pumps; at least one mechanical switching element operationally connected to the control and processing unit and to at least one of the pressure reservoirs, and at least one measuring element capable of measuring a pulse-wave or a cardiac cycle.

Unless otherwise defined, all technical and scientific terms used herein have the same meaning as commonly understood by one of ordinary skill in the art. Although methods and materials similar or equivalent to those described herein can be used in the practice or testing of the embodiments, suitable methods and materials are described below. In case of conflict, the specification, including definitions, will control. In addition, the materials, methods, and examples are illustrative only and not intended to be limiting.

BRIEF DESCRIPTION OF THE DRAWINGS

With specific reference now to the drawings in detail, it is stressed that the particulars shown are by way of example and for purposes of illustrative discussion of the preferred embodiments only, and are presented in the cause of providing what is believed to be the most useful and readily understood description of the principles and conceptual aspects of the invention. In this regard, no attempt is made to show structural details in more detail than is necessary for a fundamental understanding of the invention.

In the drawings:

FIG. 3A shows the system from FIG. 1 with a closed fluid pressure system in a positive pressure phase, according to an exemplary embodiment.

FIG. 3B shows the system from FIG. 1 with a closed fluid pressure system in a negative pressure phase, according to an exemplary embodiment.

FIG. 4A shows the system from FIG. 1 with two or more contiguous annular cuffs in a positive pressure phase, according to an exemplary embodiment.

FIG. 6A shows the system of FIG. 5A with two or more contiguous annular cuffs, according to an exemplary embodiment.

FIG. 7A shows the system of FIG. 5A with predetermined levels of force mechanically exerted to an outside surface of the penis, according to an exemplary embodiment.

FIG. 8A shows the system of FIG. 7A with a one way valve, according to an exemplary embodiment.

FIG. 8B shows the system of FIG. 7B with a one way valve, according to an exemplary embodiment.

FIG. 9 illustrates various patterns of positive and negative applied pressure or force application, in relation to a systemic arterial pulse-wave signal: Negative pressure is applied during a period of rapid ejection; negative pressure is applied during a period of a ventricular systole up until the dichrotic notch; negative pressure is applied during the entire period of ventricular systole, and negative pressure is applied during the systolic upstroke, and thereafter more rapid positive and negative pressure oscillations are applied until the start of the next pulse-wave.

DESCRIPTION OF PREFERRED EMBODIMENTS

Figure 1:
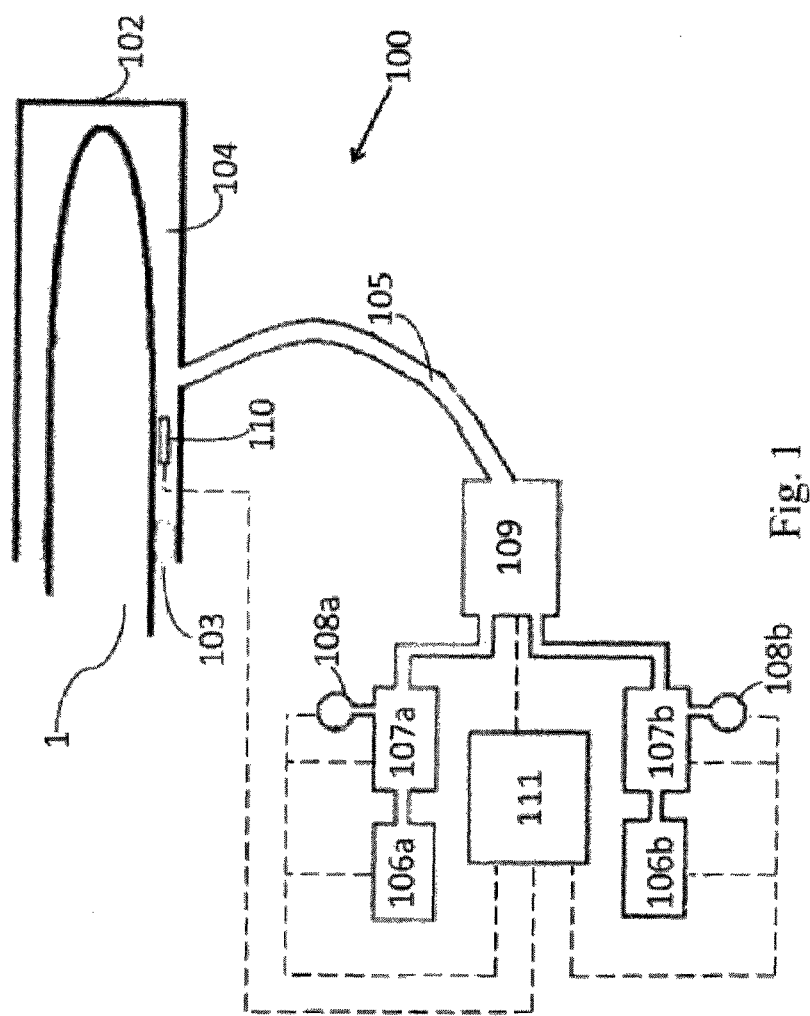
FIG. 1 schematically illustrates an externally applied system for use in the treatment of conditions resulting in or developing into erectile dysfunction, according to an exemplary embodiment.

Before explaining at least one embodiment, it is to be understood that the invention is not limited in its application to the details of construction and the arrangement of the components set forth in the following description or illustrated in the drawings. The invention encompasses other embodiments or may be practiced or carried out in various ways. Also, it is to be understood that the phraseology and terminology employed herein is for the purpose of description and should not be regarded as limiting.

For clarity, non-essential elements were omitted from some of the drawings.

The present invention is based on systems and methods utilizing externally applied apparatus for delivering pulses of pressure fluctuations, or mechanical perturbations to the penis, including the penile blood vessels and sponge like erectile tissues unique to the penis (principally the corpora cavernosa and corpus spongiosum), for the treatment of conditions resulting in or developing into erectile dysfunction, and provides substantial improvements over previous methods and apparatus for this purpose when either being used alone or in conjunction with other therapeutic modalities The blood volume excursions brought about by the embodiments involve the application of both sub-atmospheric pressure and supra-atmospheric pressure or applied mechanical force to the penile tissue mass during the treatment, to augment the inflow and outflow of blood into the blood vessels and most importantly, the highly distensible and compliant spongy tissues uniquely characteristic of the penis, resulting in substantially greater induced volume and flow swings than would be achievable by either positive or negative applied force alone.

The methods and systems are preferably designed to operate in relation to and in concert with the cyclic activity of the systemic circulatory system, wherein the timings of the applied pressures or applied forces are based on peripheral arterial blood pulse waves.

In addition, the timing may also be applicable in a manner which is paced at a higher rate than the fundamental pulse-rate or a rate which operates in synchrony with the pulse wave during the systolic period of the pulse wave and at a higher rate during the remainder of the cardiac cycle.

The underlying advantage of the current invention lies in the application of both sub-atmospheric pressure and supra-atmospheric pressure or applied mechanical force, to the penile tissue mass during the treatment, to optimally augment the inflow and outflow of blood into the blood vessels, and most importantly, to the highly distensible and compliant spongy tissues of the penis, resulting in substantially greater induced volume and flow swings with each such cycle.

The ability to utilize both positive and negative pressures to augment the inflow and outflow of blood into the blood vessels and the spongy tissues of the penis is made possible by its unique histological and structural characteristics, foremost being that of its large proportion of spongy tissues, which is not characteristic of the systemic circulation in general.

In the particular case of the penis, initial application of negative pressure to the tissue mass greatly augments the treatment effect of subsequent applied positive pressure (as explained in detail below), because the filling of the corpora cavernosa, and vascular distention, ahead of the positive counter-pressure phase would greatly increase the extent of shear stress, and the tendency to dilate collateral vessels produced during the subsequent application of positive counter pressure, due to the increased magnitude of the transient induced flows generated.

This phenomenon would apply in both the arterial and venous arms of the circulation, and would be most particularly effective well in the highly distensible tissues corpora cavernosa and corpus spongiosum, where it would be extremely effective in view of the compliant nature of these tissues.

FIG. 1 schematically illustrates a system (100) externally applied for use in the treatment of conditions resulting in or developing into erectile dysfunction, according to an exemplary embodiment.

The system 100 comprises: a socket 102; circumferential sealing means 103 at an open end of the sleeve, which when placed around a penis 1 defines a compartment 104 between the outside surface of the penis 1 and the inside surface of the socket 102; pulse sensing elements 110; two pressure reservoirs 107a, 107b fluidly connected to the compartment; feedback controlled pumps 6a, 6b; pressure transducers 108a, 108b; fast mechanical switching elements 109; a control and processing unit 111 operationally connected to the pumps 106, pressure transducer 108, elements 109 and sensing elements 110. Switching pumping modes is gated by either the subjects systemic pulse signal, ECG, or a volume related signal derived from the tissues being treated, as detected by pulse sensing elements 110.

This system 100 may thus deliver pulses of pressure fluctuations, or mechanical perturbations to the penis 1, including the penile blood vessels, using a regimen similar to the EECP used on lower limbs in severe coronary artery disease (CAD), and peripheral artery disease (PAD).

EECP (Enhanced External Counter Pulsation), which was introduced several decades ago, is based on the application of external positive pressure using multiple cuffs (usually three, with each on the calves, thighs and buttocks), applied to the lower limbs in synchrony with the patient's ventricular ejection phase of the cardiac cycle.

Clinical benefits of the EECP method have been reported as including improvement in such clinical entities as ischaemic heart disease with or without left ventricular dysfunction, reduction of heart failure of any aetiology, improved perfusion in vascular beds, prolongation of the time to exercise-induced ST-segment depression, resolution of myocardial perfusion defects, and enhanced exercise tolerance and quality of life.

While the actual mechanism by which EECP exerts its beneficial clinical effects has not been fully elucidated, several potential mechanisms are considered to be potentially involved, including the induction of higher shear stress acting on the endothelium due to increased blood flow velocity, which improves endothelial function by increasing nitric oxide, reducing endothelin, inhibiting inflammatory cytokines, and promoting collateralization, angiogenesis, and enhanced cellular metabolism. The applied counter pressure also causes a retrograde pulse of blood which can induce a mechanical dilation of collateral vessels, and thus promote collateralization.

Based on current physiological knowledge, a common link may be postulated to underlie all of the above mentioned mechanisms by which EECP exerts its beneficial effects. This is the induced surge of blood flow brought about by the applied counter-pressure, which results in a state of transient elevated shear stress acting on the endothelial lining of the vascular walls, and elicits an increase of vasodilatory factors notably NO, a factor which also promotes angiogenesis. The applied counter pressure also causes a retrograde pulse of blood which can induce a mechanical dilation of collateral vessels, and thus promote collateralization.

For application of pressure to blood vessels in synchronization to the heart rate, it may be helpful to determine the derivative of the detected pulse signal in order to more accurately determine the points in time at which the respective event in the peripheral pulse wave cycle has occurred. As examples of this, the point of zero crossing, (from positive to negative) of the first derivate of the signal would accurately represent the systolic peak, while the preceding peak would represent the point of maximal arterial filling rate. Utilizing the information from the pulse signal may be helpful in optimizing the effectiveness of the respective pressure applications, since it could be used to optimally facilitate the dilation of blood vessels and filling of the spongy tissues in relation to the peripheral pulse-wave cycle, and likewise optimize the emptying of the spongy tissues and collapse of the blood vessels, after ventricular ejection and aortic stretching have ceased.

In contrast to the known EECP method and system, which applies pulses of positive pressure to the body surface in an oscillatory manner to compress the blood vessels, the system and method use both sub-atmospheric (negative) pressure and supra-atmospheric (positive) pressure pulsations, to augment the inflow of blood into the arteries of the penis subsequent to their compression. The improvement beneficially results in substantially greater induced volume and flow swings. The system may be configured to either applying external pressure, or mechanically induced deformations of the treated tissues, or a combination of both.

The system 100 may be configured to allow further applying a span of pressures ranging from a sub-atmospheric pressure level sufficient to produce patency of the blood vessels (a state of vascular dilation), which serves to allow and actively enhance the inflow of blood into the arteries of the penis (1), up to a positive pressure level sufficient to produce a state of collapse of the blood vessels, and enhanced compression and emptying of the spongy tissues from blood. The benefit of such a broad range of blood vessel caliber changes is that it results in far larger induced blood volume changes within the blood vessels, and thereby greatly increases the beneficial clinical effects.

The system may be programmed to allow applying a negative pressure which may be applied prior to applying the conventional positive counter pressure used in EECP therapy. Since such applied negative pressure is physically the opposite of applied positive pressure, it might therefore be reasonable to expect it to have the opposite effect on blood vessels, and its use might thus appear to run counter to the accepted method of EECP, or perhaps even be construed as opposing the benefit of the applied counter-pressure. Despite this apparent contradiction, this appears not to be the case, as the described method may improve blood flow specifically to the penis, while not improving flow to the heart of the user (as achieved with the EECP method).

The ability to utilize both positive and negative pressures or mechanically applied tissue deformations, to augment the inflow and outflow of blood into the blood vessels and the erectile spongy tissues of the penis is made possible by its unique histological and structural characteristics, foremost being that of its large proportion of erectile spongy tissues which is not characteristic of the systemic circulation in general. Therefore in the particular case of the penis, the initial application of negative pressure to the tissue mass would in fact greatly augment the beneficial treatment effect of subsequent applied positive pressure, because the filling of the corpora cavernosa and vascular distention ahead of the positive counter pressure phase would greatly increase the extent of shear stress. Furthermore, an additional reason may be the tendency to dilate collateral vessels produced during the subsequent application of positive counter pressure, due to the increased magnitude of the transient induced flows generated.

It is thought that after increased blood volume is created in the penile vasculature, connective tissues, and the tissues comprising the corpora cavernosa and corpus spongiosum, the vascular beds of these tissues are passively dilated by negative pressure, resulting in vascular distention ahead of the counter pressure phase. The negative pressure application magnifies the extent of shear stress and the tendency to dilate collateral vessels during the subsequent application of counter pressure, due to the increase of the transient induced flows generated. This phenomenon would apply in arterial and venous arms of the circulation, as well as the in the highly distensible vascular beds of the corpora cavernosa and corpus spongiosum, where it would be extremely effective in view of the compliant nature of these tissues.

Many technical approaches may be utilized for effecting the induction of blood vessel caliber and spongy tissue volume changes. The broad categories include:

Fluid pressure systems for applying positive or sub atmospheric pressure directly to the surface of the penis, wherein the pressure generating means is not a closed system, as will be explained below.

Systems which apply pressure to the surface of the penis via a membrane which is part of a closed fluid pressure system.

Mixed open and closed fluid pressure application systems

Mechanical tissue deformation systems.

Within each of the above listed categories numerous possible designs may be envisaged, and for purposes of description, only samples are described for each category to illustrate the basic principles of operation involved.

The fluid tightness of such the system 100 depends on the effectiveness of the circumferential sealing means 103. The cylindrical socket 102 is configured to surround and enclose the penis 1 and to form a seal to the body of the penis 1 sufficient to enable pressure gradients to be established in the space between the outside surface of the penis 1 and the inside surface of the said cylindrical socket 102. the pressure between the outside surface of the penis 1 and the inside surface of a cylindrical connecting socket 105 may be switched by an instruction from the controller 111 between the reservoirs 107*a*, 107*b*, each connected to at least one pressure transducer 108*a*, 108*b*, wherein respective predetermined negative and positive pressure levels are set by the feedback controlling pumps 106*a*, 106*b* as a pressure manipulation mechanism. The peripheral pulse-wave may be measured with the pulse measuring elements 110 at the genitals where a peripheral pulse is specific for the blood vessels in the penis 1. The pressure application may be time delayed by a fixed pre-determined value relative to the peripheral pulse-wave cycle to optimize blood flow, or may be otherwise modulated with respect to the subjects' pulse.

The manner and timing in which the system 100 applies external positive and negative pressure and/or force can be coordinated in numerous ways with respect to the peripheral pulse-wave cycle. In one particular pattern of timing, the negative pressure application can be timed to begin at the onset of the systolic upstroke as detected by a locally recorded pulse signal (e.g. a photo-plethysmographic signal), or at a fixed time delay from the ECG-R wave sufficient for the ejected blood to reach the penis 1, so as to augment the filling of the tissues with blood during the systolic phase. Furthermore, the synchronization may continue for a predetermined time period, or until a predetermined fraction of the cardiac or peripheral pulse wave cycle, for example the systolic peak, or the dichrotic notch (or incisura), has been reached whereupon a period of pressure holding, or the initiation of positive pressure application may begin. The use of a local pulse signal as the trigger is particularly helpful since certain pulse landmarks represent physiologically relevant points in the peripheral pulse-wave cycle. As examples of this, the peak of the pulse signal upstroke (systolic peak), signifies the peak filling volume of the artery, while the dichrotic notch (or incisura), represents the termination of the period of ventricular systole. Either of these pulse landmarks may be used to mark the point of transition from applying negative to applying positive pressure. A further alternative may be to use the detected pulse signal of the local tissue volume, to determine a preset level of local tissue volume, or a preset fraction of the upstroke amplitude on either the upstroke or down stroke of the signal, or a preset level of filling rate, to mark the end of negative pressure application.

While the use of feedback related to the systemic peripheral pulse-wave cycle may be used to great advantage in coordinating the timing and magnitude of the applied positive and negative pressure applications as described above, in the case of penis erectile dysfunction it is also possible to bypass this mode of operation, and apply pressure changes independently of the activity of the peripheral pulse-wave cycle, since the substantial modulation of blood volume may be effected in the compliant and highly distensible tissues unique to the penis. Thus pressure swings at a frequency greater than the pulse rate and may exert even greater therapeutic effects.

The system 100 depicted in FIG. 1 may be configured to allow generating multiple levels of fluid pressure. For instance, pumps 106a or 106b may be used to supply multiple pressure reservoirs 107a, 107b by using pressure feedback control to activate an array of solenoid switches. Alternatively, a controllable fluid pressure generating system could be based on the use of a rapidly adjustable pressure feedback controlled variable displacement syringe in lieu of the system illustrated in FIG. 1.

Figure 2:
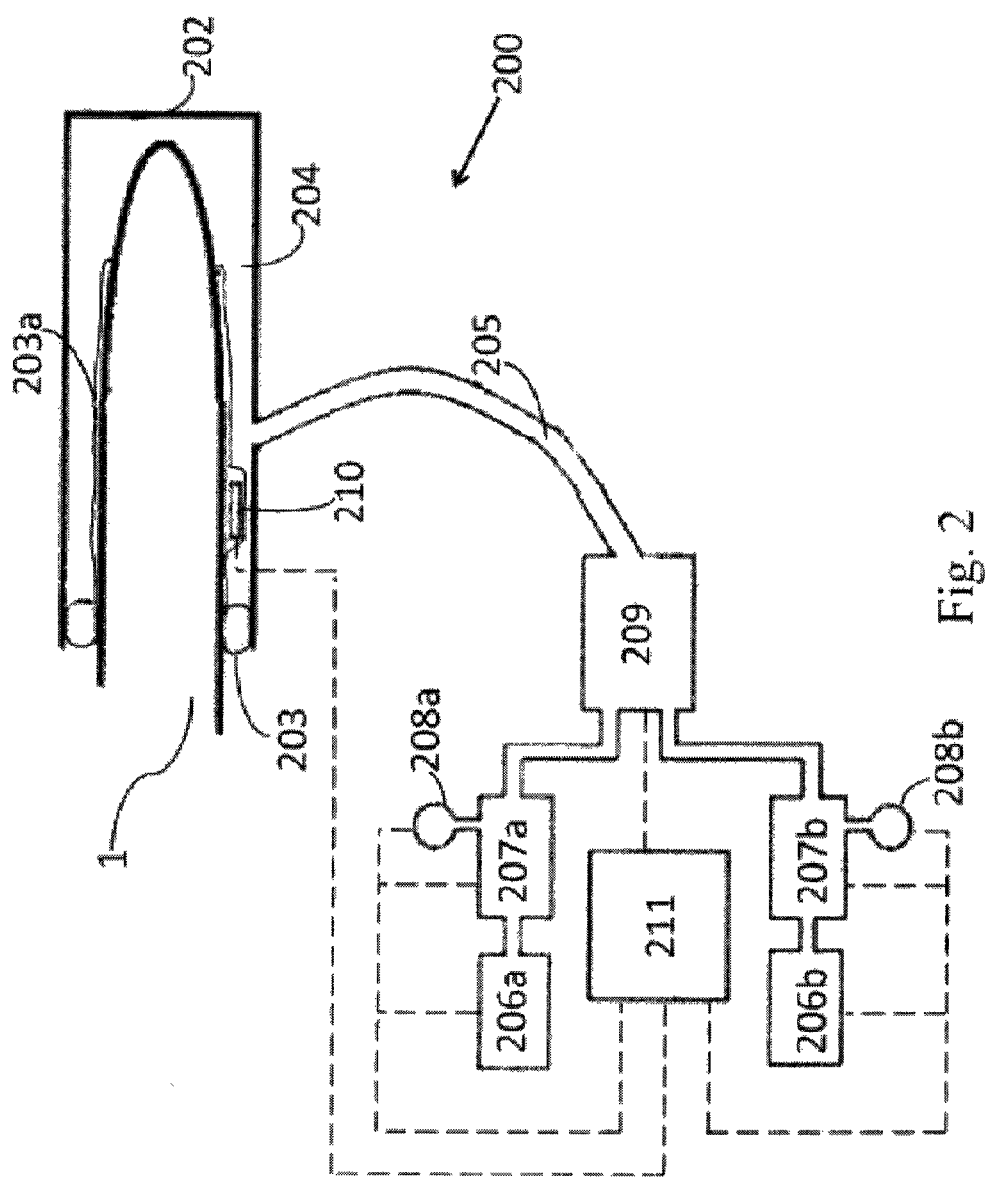
FIG. 2 shows the system from FIG. 1 with a sleeve like extension, according to an exemplary embodiment.

In the system illustrated in FIG. 1, sealing of the system 100 is achieved by a circumferential seal 103. Inadequate sealing may compromise the effectiveness of the applied pressure if a leak occurs in the seal 103 to the tissue surface, particularly during the application of positive pressure. By incorporating a circumferential sleeve like extension 203a to the seal 203, as illustrated in FIG. 2, the robustness of the sealing may be considerably enhanced, wherein the circumferential sleeve-like extension 203a is connected to the pulse sensing element 210. The further addition of an adhesive (not shown) to the surface of the sleeve like extension 203a, to actively adhere to the patient skin surface, may still further improve the sealing.

The sleeve like extension 203a may be a partial sleeve as illustrated, or may be configured to completely surround the entire treated tissue (in which case it would resemble a condom). In either configuration, holes perforating the layer of the sleeve like extension 203a may be provided to avoid any trapping of air between the skin surface and the sleeve like extension 203a.

While the "open" systems 100, 200 shown in FIGS. 1 and 2 enable both positive and negative pressures to be applied within the compartment space 104, 204 between the penis 1 and the case of socket 102, 202, this type of system may be susceptible to leakage, especially when positive pressure is being applied. This tendency would be smaller during negative pressure application, during which a self-sealing effect is brought about by the applied negative pressure urging the tissues of the penis 1 to more firmly contact the seal 103, 203 and thereby reducing the possibility of fluid leakage.

An example of a closed fluid pressure system is seen in FIGS. 3A and 3B, which depict a pressure applicator unit 300 comprising a cylindrical socket 322, with a circumferential sealing means 323 at its open end, which when placed around the penis 1, defines a compartment 324 between the outside surface of the penis 1 and the inside surface of the socket 322. Within compartment 324 there is disposed an inflatable annular cuff 319, composed of a fluid tight and highly compliant material, which is configured to enclose effectively the full tissue mass of the penis 1 when it is positively pressurized. This annular cuff 319 is fluid-tightly connected to fluid conducting socket 325, thence to a feedback controlled pressure system consisting of a pump 326, a pressure reservoir 327, a pressure transducer 328, a pulse sensing element 320 or ECG sensing element (not shown), a control and a processing unit 321 with fast mechanical switching elements 329.

An opening in the cylindrical socket 322 leading to a one way valve 340, serves to allow air in the space between the penis 1 and inflatable annular cuff 319 to escape when the annular cuff 319 is being pressured. The one way valve 340 prevents the re-entry of air when the annular cuff 319 is deflated, thus resulting in the generation of the desired negative pressure. The generation of alternating sub-diastolic pressure fields surrounding the penis 1 may thus be achieved, and the respective levels of positive and negative pressures are controlled by pressure transducer 328 and the control and processing unit 321 with fast mechanical switching elements 329.

The pressure application can be time delayed by a fixed pre-determined value to optimize blood flow, or otherwise modulated with respect to the subjects pulse, where the negative and positive pressure phases of the above described process are illustrated in FIGS. 3A and 3B respectively.

Figure 4B:
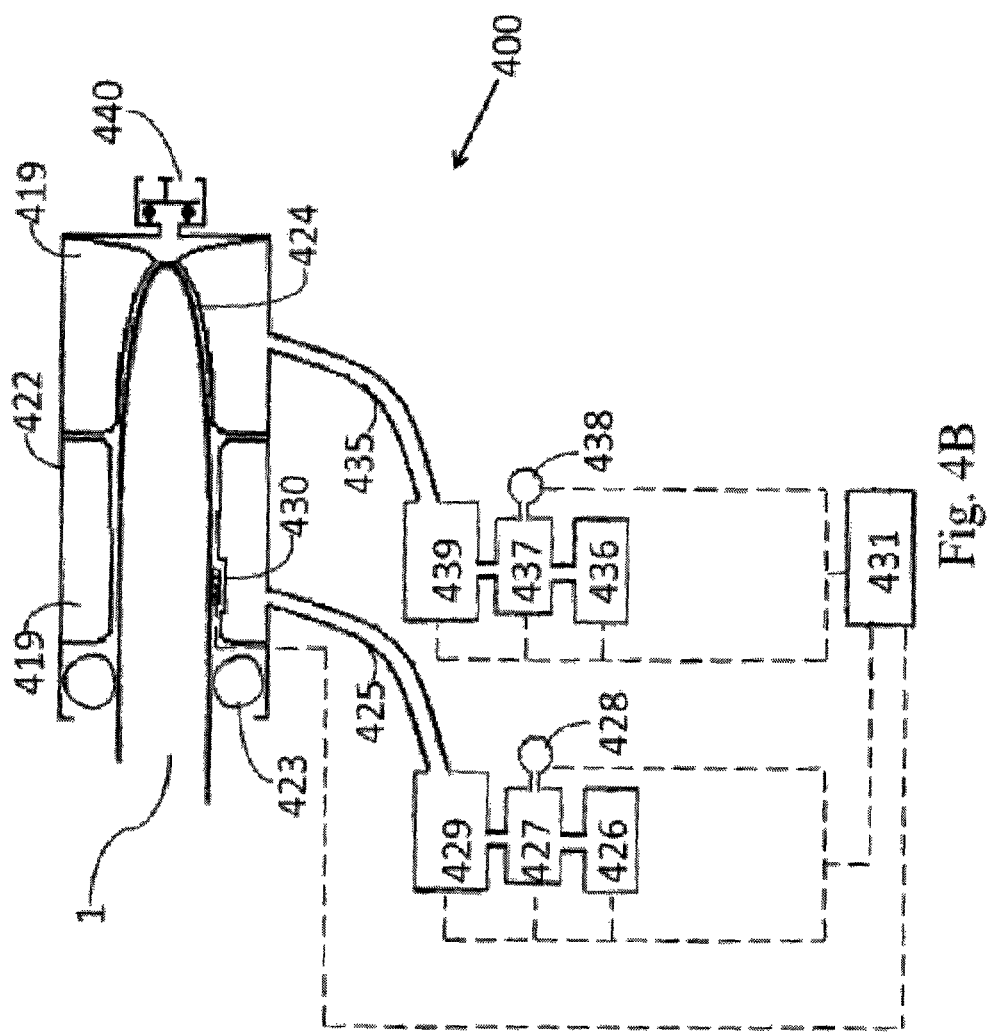
FIG. 4B shows the system from FIG. 1 with two or more contiguous annular cuffs in a negative pressure phase, according to an exemplary embodiment.

FIGS. 4A and 4B show an exemplary system 400 for a closed fluid pressure system with two or more contiguous annular cuffs 419. Each such cuff 419 is supplied by a pressure generating system as described for the single annular cuff of FIGS. 3A and 3B. The advantage of using multiple cuffs is that by appropriate sequential timing of the respective pressurization of the cuffs 419, coordinated by a processor in the control and processing unit 411, the propagation of blood in the penis's blood vessels may be controlled, and this may provide a clinically advantageous effect.

Parts 435-439 serve the same purpose as parts 425-429 respectively.

While the "closed" systems shown in FIGS. 3A, 3B, 4A and 4B, enable both positive and negative pressures to be applied within the space 424 between the penis 1, and the tubular socket 422, this embodiment may be susceptible to leakage during the negative pressure phase, despite the tendency for negative pressure to enhance sealing of the system as described. Thus although the tendency for leakage would be smaller during negative pressure application compared to during the positive pressure application, and with each phase of positive pressure any residual air would be evacuated via one way valve 440, during the transition from negative to positive pressure application there may be an increase possibility of leakage. To completely avoid such possible leaks during positive pressure application an alternative approach may be used.

FIGS. 5A, 5B, 6A and 6B, which are otherwise similar to FIGS. 3A, 3B, 4A and 4B respectively, show an additional pressure generating systems 500, 600 respectively for supplying negative pressure to the compartment 524, 624. Socket 545, 645 is attached in a fluid-tight manner to an orifice 550, 650 in the wall of cylindrical socket 522, 622 instead of a one way valve. This pressure system comprises a pump 546, 646, a pressure reservoir 547, 647, a pressure transducer 548, 648, and a control and processing unit 521, 621 with fast mechanical switching elements 549, 649.

Parts 525-529 serve the same purpose as parts 545-549 respectively.

Figure 5A:
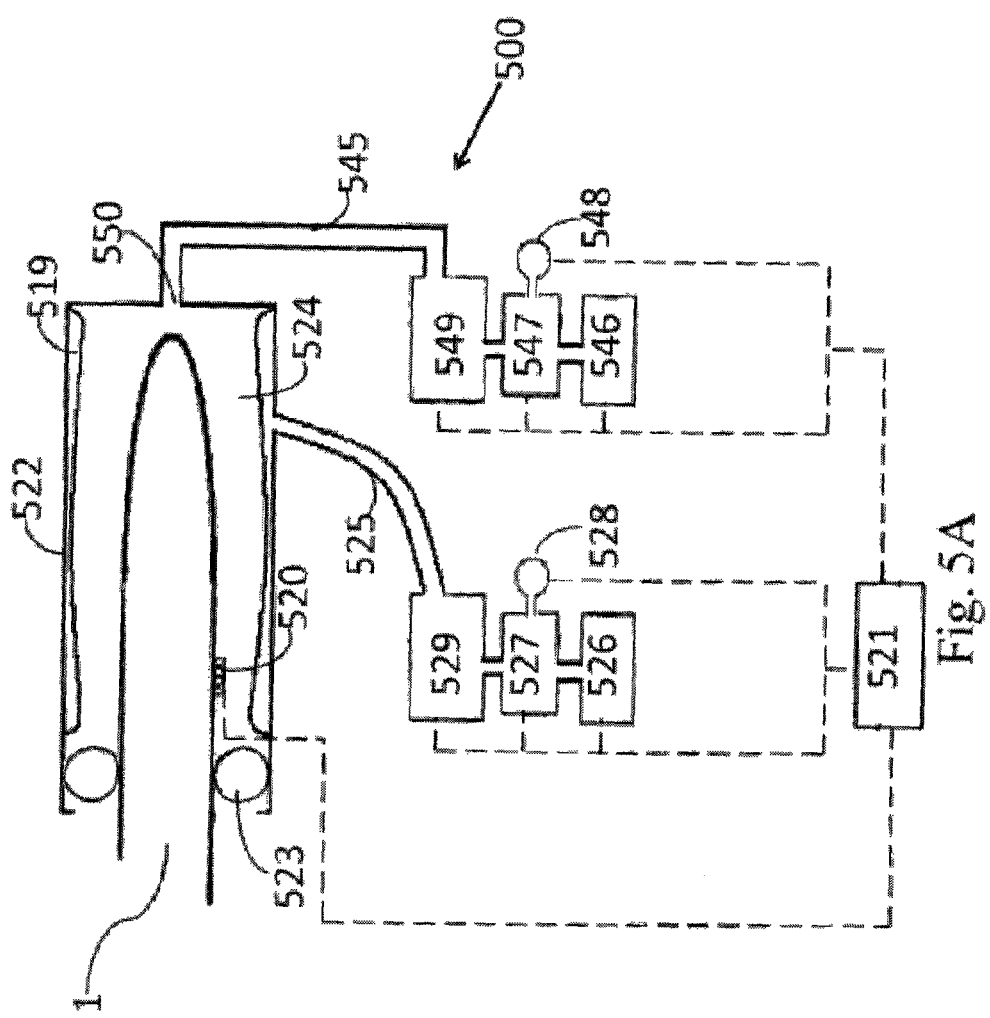
FIG. 5A shows an additional pressure generating system for supplying negative pressure to compartment outside the annular cuff in a depressurized phase, according to an exemplary embodiment.
Figure 5B:
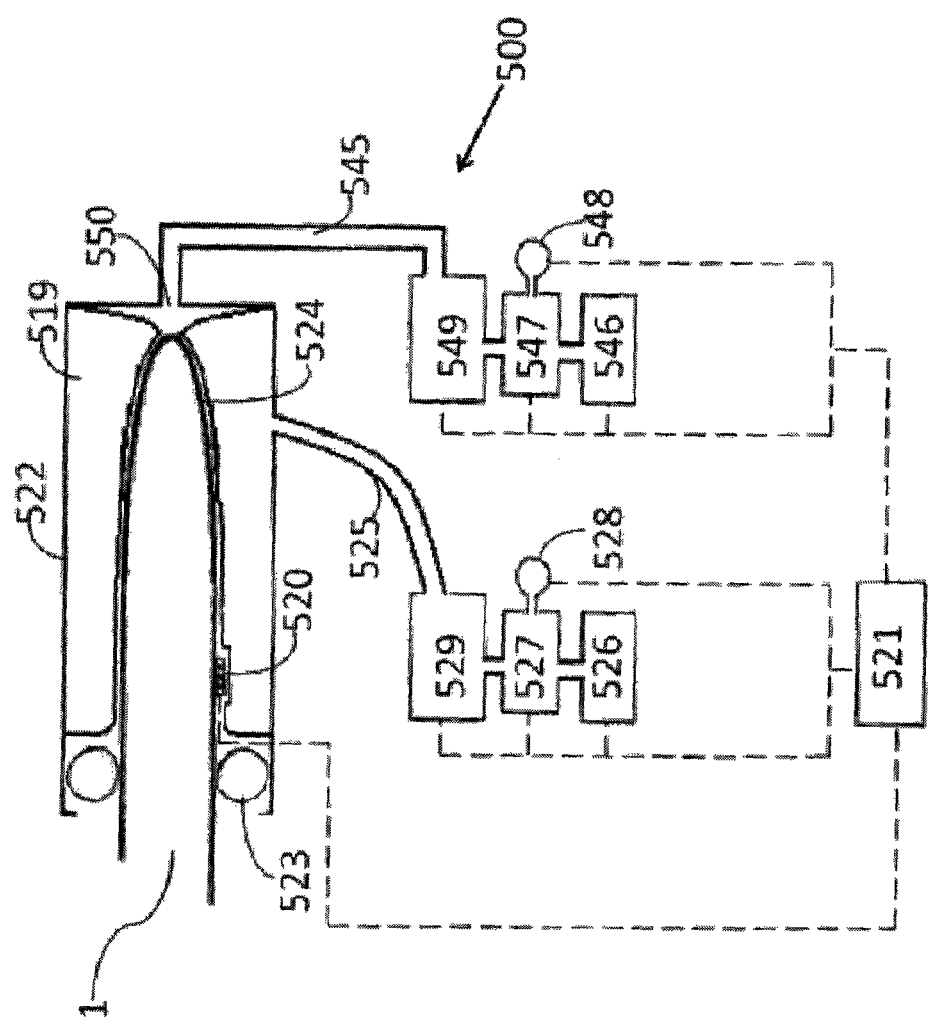
FIG. 5B shows an additional pressure generating system for supplying negative pressure to a compartment outside the annular cuff in a pressurized phase, according to an exemplary embodiment.

The action of the two systems is coordinated such that when the system supplying the annular cuff 519, 619 depressurizes the annular cuff 519, 619 as shown in FIG. 5A, the above described second system generates a negative pressure in the same manner as described in the system (100) shown in FIGS. 1 and 2, and withdraws the negative pressure as the cuff 519 is again pressurized, as illustrated in FIG. 5B. In this manner, a high level of pressurizing fluid conservation may be achieved since the positive pressure phase is fluid-lossless, while fluid loss during negative pressure application would be inherently low due to the self-sealing effect promoted by the applied negative pressure.

Parts 625-629 and 635-639 serve the same purpose as parts 645-649 respectively.

Figure 6B:
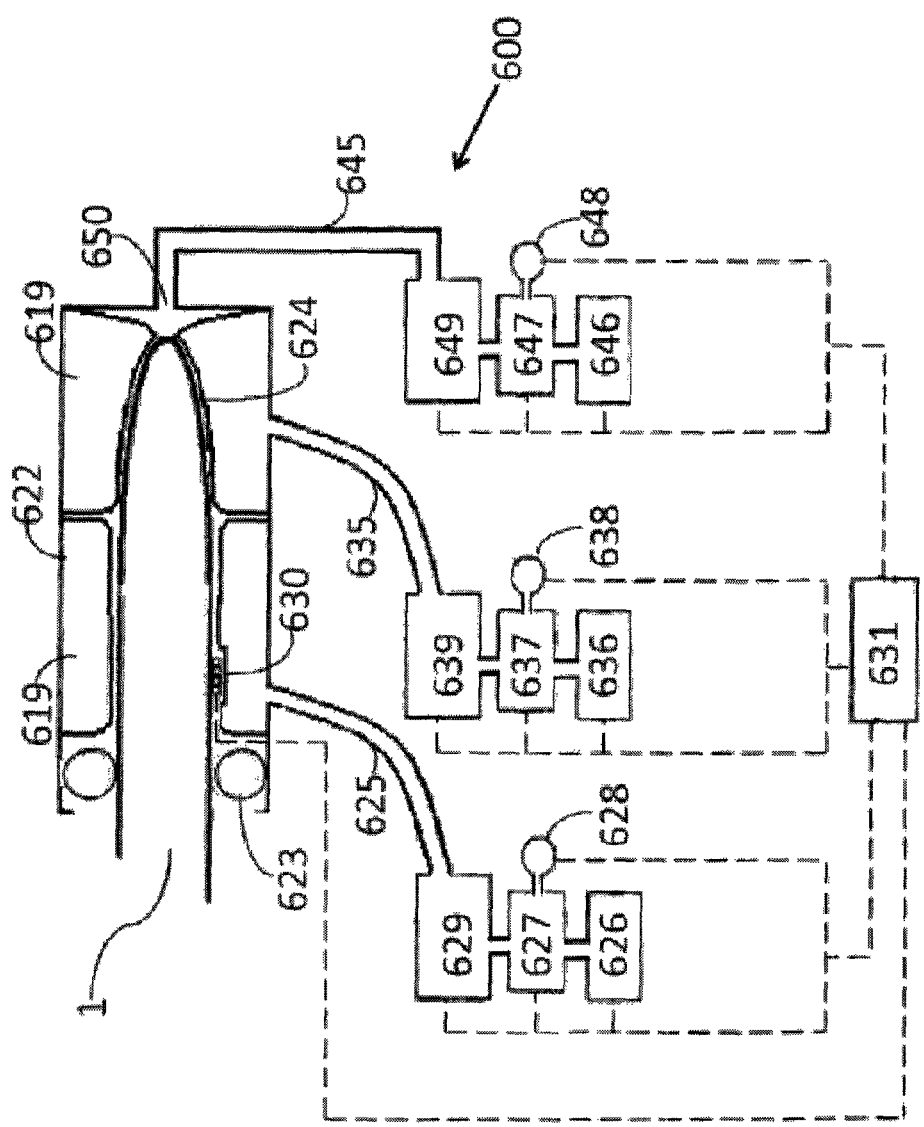
FIG. 6B shows the system of FIG. 5B with two or more contiguous annular cuffs, according to an exemplary embodiment.

Similar to FIGS. 4A and 4B, the variation of FIGS. 5A and 5B depicted in FIGS. 6A and 6B, illustrates the use of two or more adjacent annular cuffs 619 in place of a single annular cuff 619, which may facilitate sequential timing of the respective pressurization of the cuffs 619, coordinated by the processor to provide a clinically advantageous effect.

As an alternative to the fluid pressure generating systems, it is possible to also utilize systems which mechanically exert predetermined levels of force to the exterior surface of the penis 1. Illustrative examples of such systems 700, 800 respectively are shown in FIGS. 7A, 7B, 8A and 8B, having force exertion elements 751, 752, 851, 852. In these examples, surface elements such as compliant gels 751, 851 are capable of conforming to the penis contours and are mounted on rigid forms 752, 852, which have a general form corresponding to the shape of the penis 1. The force exertion elements 752, 852 are connected to mechanical means such as a linear stepper motor 753, 853, configured to allow the elements 751, 752 and 851, 852 to be urged on to the penis 1 surface to effect the collapse of the blood vessels within the penis 1. The degree of force applied by this means is under feedback control of processor unit 721, 821, which may for example use the pulse signals derived from surface pulse sensors 720*a*, 720*b*, 820*a*, 820*b*, feeding to processor and control unit 721, 821, to determine the force required to collapse the blood vessels. In the arrangement shown in these figures, the use of first and second pulse sensors 720*a*, 720*b*, 820*a*, 820*b*, wherein the first unit 720*b*, 820*b* is placed within the force field, while the second 720*a*, 820*a* is proximally placed thereto, is well suited for such an objective. Thus when sufficient force has been generated on the penis wall to cause attenuation or complete abolition of the pulse signal recorded by the second sensor 720*b*, 820*b*, relative to the signal sensed by the first sensor 720*a*, 820*a*, collapse of the blood vessel has been achieved, and no additional force need be applied. Such use of paired pulse sensors may be applicable to all the examples described in FIGS. 1, 2, 3A, 3B, 4A, 4B, 5A, 5B, 6A, 6B, 7A, 7B, 8A and 8B.

Figure 7B:
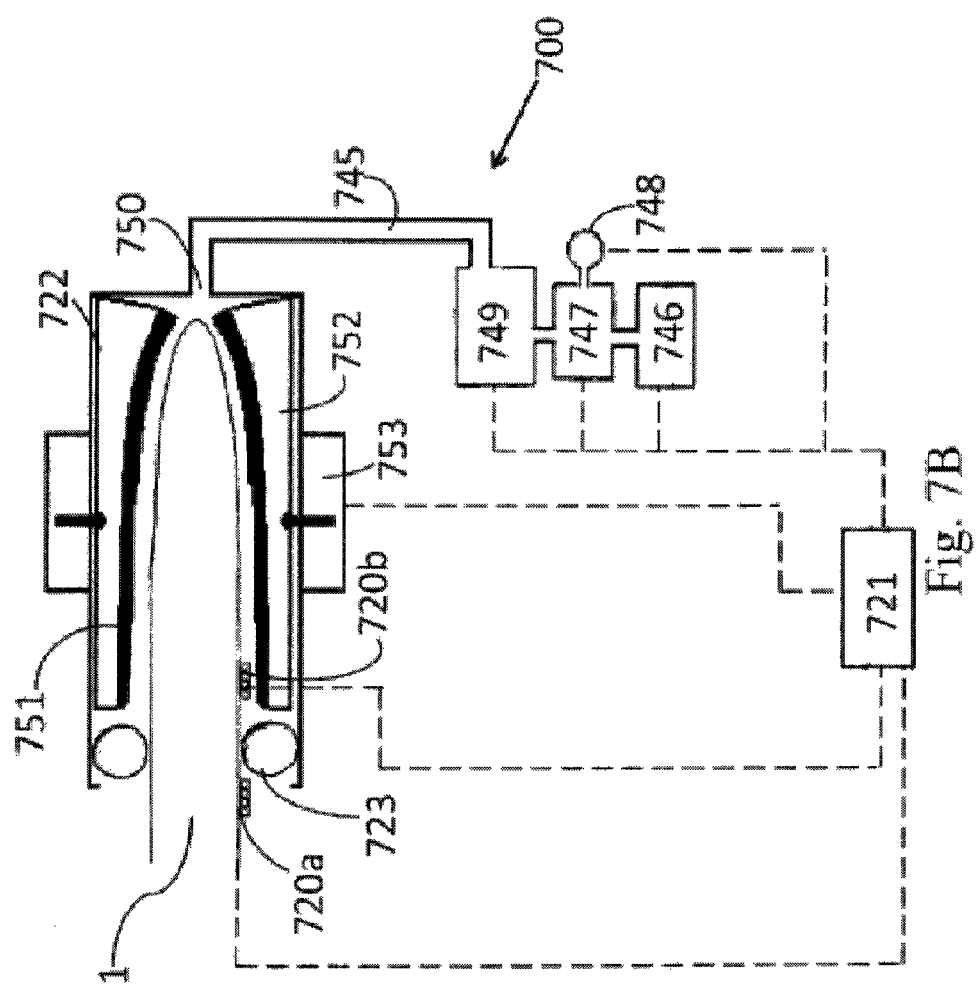
FIG. 7B shows the system of FIG. 5B with predetermined levels of force mechanically exerted to an outside surface of the penis, according to an exemplary embodiment.

For the system 700 illustrated in FIGS. 7A and 7B, the mechanical compression means is used in combination with a negative pressure generating system similar to that described in FIGS. 5A, 5B, 6A and 6B. The coordinated activity of positive force and negative applied pressure is otherwise similar to that described in the previously explained examples.

For the system 800 illustrated in FIGS. 8A and 8B, the mechanical compression means is used in combination with a one way valve similar to that described in FIGS. 3A, 3B, 4A and 4B. The force applying elements 851 and 852 are air-tightly sealed to the surrounding wall of cylindrical socket 822, by appropriately compliant sealing elements 854, such that when these elements are moved to the non-compressing position shown in FIG. 8B, a state of negative pressure occurs surrounding the penis 1, in the same manner as that described in FIGS. 3B, and 4B.

FIG. 9 schematically illustrates four representative examples of pressure patterns 920, 930, 940, 950, in relation to a systemic arterial pulse-wave signal. The detected peripheral pulse-wave 930 signal possess characteristic amplitude, shown in arbitrary units versus a time pattern. The changes of the amplitude correspond to various phases and stages of the pulse cycle, and are used to determine the manner in which the pressure or applied mechanical force 950 may be applied.

Characteristic features of the peripheral pulse-wave 930 may include: the beginning of the systolic upstroke 901; the systolic upstroke 902 which corresponds to the period of rapid ejection of the left ventricle; a time interval 907, from the systolic upstroke 901 until the systolic peak 903, corresponds to the end of the period of rapid ejection. A time period from the systolic peak 903 is a period of ventricular relaxation 908, up until the point of closure of the aortic valve at the dichrotic notch 904.

The beginning of the dichrotic notch 904, approximates the end of ventricular systole (with the overall period time interval 911), and marks the start of the diastolic phase 910, which extends to the end of the diastolic phase 905, and the start of a new systolic upstroke 901. The duration of the dichrotic notch 909 approximately corresponds to the closure of the aortic valve during which period there may be some retrograde blood flow from the aorta to the left ventricle.

An additional feature is the ability to anticipate the timing of the start of the systolic upstroke 901 of the peripheral pulse-wave 930, which may be achieved by measuring the subjects' ECG 920, and detecting the "R" wave thereof. The R wave is a particularly robust and easily measurable signal, and provides a very sharp time marker occurring at the time of peak ventricular contraction. The respective time delays 906*a*, 906*b* intervening between the R wave and the beginning of the systolic upstroke 901 and the systolic peak 905, respectively, are the time intervals during which the pulse-wave 930 propagates to the peripheral measurement site, that is the penis. The measurement of this pulse transit time, enables the delay period to be accurately estimated, and thus facilitates the advanced determination of the timing of the application of pressure 950 and/or force, as previously described.

Several possible timing schedules 960A, 960B, 960C, 960D, for effecting the application of positive and negative pressures, may be seen in FIG. 9. For instance, in 960A negative pressure is applied during the period of rapid ejection as indicated by the systolic upstroke 902, while in 960B, the negative pressure is applied during the period of the ventricular systole up until the dichrotic notch 904. In 960C, negative pressure is applied during the entire period of ventricular systole.

960D shows a pattern of pressure application during which negative pressure is applied during the systolic upstroke 902, and thereafter more rapid positive and negative pressure oscillations are applied until the start of the next pulse-wave. As can be seen from the panel of the first derivative 940 of the pulse-wave 930 signal, the detection of zero crossings can aid in the accurate determinations of the time of the systolic peak 903, and the start of the dichrotic notch 904. This is helpful in accurately determining the timing of positive and negative pressures.

As mentioned above, the predetermined delay between the ECG-R wave 920 and the various pulse-wave 930 landmarks enables the accurate determination of pressure application 950 timing to be made.

As described in the above examples a variety of sensing means such as photo-plethysmographic devices, including pulse oximeters, ECG, surface force sensors, piezo-electrical sensors, strain gauges, mercury in silastic sensors, Doppler sensors, tissue electrical impedance sensors, flow magnetometry sensors, thermal change sensors, and other means may be applied for the purpose of detecting cyclic pulsatile activity of the patient. This input is used to coordinate the timing of the treatment method, and additionally may be used to determine the level of tissue blood filling and the state of vascular filling or collapse achieved and to provide feedback for controlling the filling.

The use of paired pulse sensors wherein one unit is placed within the force or applied pressure field, while the second is placed proximally to it may be particularly advantageous in that it can be used to determine when a desired filling effect has been achieved: When further increase in volume cannot be achieved, or when sufficient force or pressure has been generated on the penis 1 wall to achieve a desired level of emptying or to cause an attenuation or complete abolition of the pulse signal.

It is appreciated that certain features of the embodiments may also be provided in combination in a single embodiment. Conversely, various features which are, for brevity, described in the context of a single embodiment, may also be provided separately or in any suitable sub combination.

Although specific embodiments have been described, it is evident that many alternatives, modifications and variations will be apparent to those skilled in the art. Accordingly, it is intended to embrace all such alternatives, modifications and variations that fall within the spirit and broad scope of the appended claims.

What invention claimed is:

1. A method of treating a condition of erectile dysfunction of a subject, the method comprising inducing cyclic augmented penile blood volume changes in the penis of the subject wherein said cyclic augmented penile blood volume changes are induced by application of alternating phases of subatmospheric pressure, and above atmospheric pressure, or mechanical force applied to the penile tissue surface, wherein said alternating of phases of sub-atmospheric pressure, and above atmospheric pressure or applied force to the penile tissues, is gated by the timing and/or amplitude and/or rate and/or shape of a peripheral pulse-wave of the subject, and wherein said pulse-wave amplitude cycle is preceded by a predetermined delay period by ECG signal markers.

2. The method according to claim 1, wherein said penile blood volume changes are penile blood vessel changes and penile erectile spongy tissue volume changes.

3. A method of treating a condition of erectile dysfunction of a subject, the method comprising inducing cyclic augmented penile blood volume changes in a penis of the subject, wherein said cyclic augmented penile blood volume changes are induced by application of alternating phases of subatmospheric pressure and above atmospheric pressure, or mechanical force applied to the penile tissue surface, said alternating phases of subatmospheric pressure and above atmospheric pressure or applied force to the penile tissue surface, is gated by timing and/or amplitude and/or rate and/or shape of a peripheral pulse-wave of the subject, and wherein said pulse-wave amplitude cycle is preceded by a predetermined delay period by ECG signal markers and wherein a time delay between said ECG signal markers and the pulse-wave amplitude cycle is determined from an estimated pulse transit time.

4. A non-invasive system for inducing penile blood vessel and penile erectile tissue volume changes, the system comprising:

a cylindrical socket having interior walls and an open end;

at least one circumferential sealing element within the cylindrical socket, wherein a pressurizable compartment is defined by the sealing element and the interior walls;

a control unit and a processing unit;

at least one pressure pump operationally connected to the control unit and the processing unit, wherein the compartment when sealed is in one of two states: a first state wherein the compartment is in positive pressure, and a second state, wherein the compartment is in sub-atmospheric pressure;

at least one pressure reservoir, each reservoir fluidly connectable to said compartment and to one of the pressure pumps;

at least one mechanical switching element operationally connected to the control unit and the processing unit and to at least one of the pressure reservoirs;

at least one measuring element capable of measuring a pulse-wave or a cardiac cycle, wherein the control unit and the processing unit are capable of receiving a signal from the measuring elements and determining a time, rate and shape of pulse-waves, and wherein said control unit and said processing unit are gated by the at least one measuring element to control said mechanical switching elements such as to switch fluid connectivity of the pressurizable compartment to the reservoirs and alternately switch the sealed compartment between the first state and the second state, and further comprising a pressure or force application controlling mechanism operationally connected to the control unit and the processing unit and the measuring elements, and programmed to control the positive pressure or applied force and sub-atmospheric pressure according to an amplitude of the measured pulse or pulse-wave.

5. The non-invasive system according to claim 4, wherein the switching of pressures is gated by the onset of a systolic upstroke as measured by said measuring element.

6. A non-invasive system for inducing penile blood vessel and penile erectile tissue volume changes, the system comprising:
- a cylindrical socket having interior walls and an open end;
- at least one circumferential sealing element within the cylindrical socket, wherein a pressurizable compartment is defined by the sealing element and the interior walls;
- a control unit and a processing unit;
- at least one pressure pump operationally connected to the control unit and the processing unit, wherein the compartment when sealed is in one of two states: a first state wherein the compartment is in positive pressure, and a second state, wherein the compartment is in sub-atmospheric pressure;
- at least one pressure reservoir, each reservoir fluidly connectable to said compartment and to one of the pressure pumps;
- at least one mechanical switching element operationally connected to the control unit and the processing unit and to at least one of the pressure reservoirs;
- at least one measuring element capable of measuring a pulse-wave or a cardiac cycle, wherein the control unit and the processing unit are capable of receiving a signal from the measuring elements and determining a time, rate and shape of pulse-waves, and wherein said control unit and said processing unit are gated by the at least one measuring element to control said mechanical switching elements such as to switch fluid connectivity of the pressurizable compartment to the reservoirs and alternately switch the sealed compartment between the first state and the second state, wherein the switching of pressures or applied force is gated by a fixed time delay from an ECG-R wave as predetermined with respect to the measuring elements.

7. The non-invasive system according to claim 4, wherein the switching is programmed to occur at a predetermined fraction of a predetermined time period from the onset of the systolic upstroke.

8. The non-invasive system according to claim 4, wherein the switching of pressures is programmed to be carried out at a rate higher than the measured pulse rate.

9. The non-invasive system according to claim 4, further comprising an inflatable annular cuff fluidly connected to said at least one pressure pump.

10. The non-invasive system according to claim 4, further comprising at least two inflatable annular cuffs fluidly connected to said at least one pressure pump, or at least one force applying means, and capable of sequential timing of the respective pressurization of the cuffs, coordinated by said processor in the control and processing unit.

11. The non-invasive system according to claim 4, further comprising a circumferential sleeve-like extension to the sealing element, wherein the circumferential sleeve-like extension is connected to the at least one measuring element.

12. The non-invasive system according to claim 4, wherein said at least one measuring element comprises a first pulse sensor and a second pulse sensor wherein the first pulse sensor is placed within the compartment, and the second pulse sensor is placed outside the compartment, and the control unit is programmed such that when a desired level of emptying or an attenuation or complete abolition of the pulse signal is recorded by the first sensor, relative to the signal recorded by the second sensor, the control unit commands the pumps to cease applying positive pressure or force to the compartment.

13. The non-invasive system according to claim 4, wherein said at least one measuring element comprises a first pulse sensor and a second pulse sensor wherein the first pulse sensor is placed within the compartment, and the second pulse sensor is placed outside the compartment, and the control unit is programmed such that when an amplitude of a pulse signal is recorded by the first sensor exceeds a predetermined value, relative to the signal recorded by the second sensor, the control unit commands the pumps to cease applying sub-atmospheric pressure to the compartment.

14. A non-invasive system for inducing penile blood vessel and penile erectile tissue volume changes, the system comprising:
- a cylindrical socket, having interior walls and an open end;
- at least one circumferential sealing element within the socket,
- wherein a compartment is defined by the sealing element and the interior walls;
- a control unit and a processing unit;
- a linear stepper motor connected to said control unit and the processing unit;
- at least one force exertion element capable of applying force onto said interior walls;
- a one-way valve connectable to said compartment and capable of removing air trapped by said at least one force exertion element;
- at least one measuring elements capable of measuring a pulse-wave or a cardiac cycle, wherein the control unit and the processing unit are capable of receiving a signal from the measuring elements and determining a time, rate and shape of pulse-waves, and wherein said control unit and said processing unit are gated by the at least one measuring element to control said linear stepper motor.

15. The non-invasive system according to claim 14, wherein said at least one measuring element comprises a first pulse sensor and a second pulse sensor wherein the first pulse sensor is placed within the compartment, and the second pulse sensor is placed outside the compartment, and the control unit is programmed such that when a desired level of emptying or an attenuation or complete abolition of the pulse signal is recorded by the first sensor, relative to the signal recorded by the second sensor, the control unit commands the force exertion element to cease applying positive pressure or force to the compartment.

16. A non-invasive system for inducing penile blood vessel and penile erectile tissue volume changes, the system comprising:
- a cylindrical socket having interior walls and an open end;
- at least one circumferential sealing element within the socket,
- wherein a compartment is defined by the sealing element and the interior walls;
- a control unit and a processing unit;
- a linear stepper motor, connected to said control unit and said processing unit;
- at least one force exertion element capable of applying force onto said interior walls;
- at least one pressure pump operationally connected to the control and processing unit;
- at least one pressure reservoir, each reservoir fluidly connectable to said compartment and to one of the pressure pumps;

at least one mechanical switching element operationally connected to the control unit and the processing unit and to at least one of the pressure reservoirs;

at least one measuring element capable of measuring a pulse-wave or a cardiac cycle, wherein the control unit and the processing unit is capable of receiving a signal from the measuring elements and determining a time, rate and shape of pulse-waves, and wherein said control unit and said processing unit is gated by the at least one measuring element to control said linear stepper motor and said at least one pressure pump.

17. The non-invasive system according to claim 16, wherein said at least one measuring element comprises a first pulse sensor and a second pulse sensor wherein the first pulse sensor is placed within the compartment, and the second pulse sensor is placed outside the compartment, and the control unit is programmed such that when a desired level of emptying or an attenuation or complete abolition of the pulse signal is recorded by the first sensor, relative to the signal recorded by the second sensor, the control unit commands the pumps to cease applying positive pressure or force to the compartment.

18. Inducing cyclic augmented penile blood volume changes in a penis of a subject comprising:

providing a cylindrical socket having interior walls, an open end, at least one circumferential sealing element within the socket, a means for inducing cyclic augmented penile blood volume changes in the penis of the subject; wherein a pressurizable compartment is defined by the sealing element and the interior walls; a control unit and a processing unit; at least one mechanical switching element operationally connected to the control unit and the processing unit and at least one measuring element capable of measuring a pulse-wave or a cardiac cycle;

sealing the compartment by inserting the penis through the sealing element into the socket;

operationally coupling the measurement elements to the subject;

sending at least one signal from the measuring elements to the control unit and the processing unit, and determining a time, rate and shape of pulse-waves from the subject;

the at least one measuring element gating said control unit and the processing unit to alternately apply with the means for inducing cyclic augmented penile blood volume changes, such as to apply positive force or pressure to the penis, and sub-atmospheric pressure to said compartment, such as to apply sub-atmospheric pressure to the penis, wherein said alternating of phases of sub-atmospheric pressure, and above atmospheric pressure or applied force to the penile tissues, is gated by the timing and/or amplitude and/or rate and/or shape of a peripheral pulse-wave of the subject, and wherein said pulse-wave amplitude cycle is preceded by a predetermined delay period by ECG signal markers.

19. The inducing of claim 18, wherein said means for inducing cyclic augmented penile blood volume changes in the penis of the subject is an at least one pressure pump operationally connected to the control unit and the processing unit;

the providing a cylindrical socket further comprising providing of at least one pressure reservoir, each reservoir fluidly connectable to said compartment and to one of the pressure pumps; at least one mechanical switching element operationally connected to the control and processing unit and to at least one of the pressure reservoirs, and at least one measuring element capable of measuring a pulse-wave or a cardiac cycle.

20. The inducing of claim 18, wherein said means for inducing cyclic augmented penile blood volume changes in the penis of the subject is at least one force applicator operationally connected to the control unit and the processing unit, and at least one pressure pump operationally connected to the control unit and the processing unit;

the providing a cylindrical socket further comprising providing of at least one pressure reservoir, each reservoir fluidly connectable to said compartment and to one of the pressure pumps; at least one mechanical switching element operationally connected to the control and processing unit and to at least one of the pressure reservoirs, and at least one measuring element capable of measuring a pulse-wave or a cardiac cycle.

* * * * *